United States Patent
Galgalkar et al.

(10) Patent No.: US 11,460,475 B2
(45) Date of Patent: Oct. 4, 2022

(54) COMPOSITION OF A BILIRUBIN STOCK AND A METHOD OF PREPARATION THEREOF

(71) Applicant: Siemens Healthcare Diagnostics Inc., Tarrytown, NY (US)

(72) Inventors: Sudipa Galgalkar, Bangalore (IN); Ishita Chakraborty, Bangalore (IN); Ragavendar Ms, Flanders, NJ (US); David Ledden, Elkhart, IN (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 0 days.

(21) Appl. No.: 17/265,964

(22) PCT Filed: Jul. 31, 2019

(86) PCT No.: PCT/US2019/044359
§ 371 (c)(1),
(2) Date: Feb. 4, 2021

(87) PCT Pub. No.: WO2020/033200
PCT Pub. Date: Feb. 13, 2020

(65) Prior Publication Data
US 2021/0382074 A1    Dec. 9, 2021

Related U.S. Application Data (60) Provisional application No. 62/716,557, filed on Aug. 9, 2018.

(51) Int. Cl.
*G01N 33/72* (2006.01)
*G01N 1/38* (2006.01)
*G01N 1/28* (2006.01)

(52) U.S. Cl.
CPC ............... *G01N 33/72* (2013.01); *G01N 1/38* (2013.01); *G01N 33/728* (2013.01); *G01N 2001/2893* (2013.01); *G01N 2496/00* (2013.01); *Y10T 436/103332* (2015.01)

(58) Field of Classification Search
CPC ............. G01N 1/38; G01N 2001/2893; G01N 2496/00; G01N 33/72; G01N 33/728; Y10T 436/10; Y10T 436/103332; Y10T 436/171538
USPC .............................. 436/8, 12, 108; 252/408.1
See application file for complete search history.

(56) References Cited

U.S. PATENT DOCUMENTS

| 3,477,818 A | 11/1969 | Fried et al. |
| 4,260,579 A | 4/1981 | Barton et al. |
| 5,869,276 A * | 2/1999 | Kojima ............... C12Q 1/26 435/961 |
| 6,696,297 B2 | 2/2004 | Seizew et al. |

FOREIGN PATENT DOCUMENTS

| CN | 106771112 B | 8/2018 |
| WO | 2011145110 A1 | 11/2011 |
| WO | 2015155753 A2 | 10/2015 |

OTHER PUBLICATIONS

European Search Report and Search Opinion of European Patent Application No. 19848308.3 dated Nov. 29, 2021.
International Search Report and Written Opinion of International Application No. PCT/US2019/044359 dated Oct. 15, 2019.
Tam et al., "Bilirubin Inhibits Calcium Carbonate Precipitation In Gallbladder Bile", Surgery, Sep. 1995, vol. 118, No. 3; pp. 1-3.
Weisiger et al., "Affinity of Human Serum Albumin for Bilirubin Varies with Albumin Concentration and Buffer Composition", The Journal of Biological Chemistry, Aug. 10, 2001, vol. 276, No. 32; pp. 29953-29960.
Hulzebos et al., "The Bilirubin Albumin Ratio in the Management of Hyperbilirubinemia in Preterm Infants to Improve Neurodevelopmental Outcome: A Randomized Controlled Trial—BARTrial", PLOS One, Jun. 2014, vol. 9, No. 6, pp. 1-6.
Ahlfors, Charles E., "The Bilirubin Binding Panel: A Henderson-Hasselbalch Approach to Neonatal Hyperbilirubinemia", Pediatrics, Oct. 2016, vol. 138, No. 4, pp. 1-11.
Amin et al., "Bilirubin Albumin Binding and Unbound Unconjugated Hyperbilirubinemia in Premature Infants", J Pediatr. Jan. 2018, vol. 192; pp. 1-11.
Boon et al., "Endogenously Elevated Bilirubin Modulates Kidney Function and Protects From Circulating Oxidative Stress in a Rat Model of Adenine-Induced Kidney Failure", Scientific Reports, Oct. 26, 2015, vol. 5, pp. 1-16.
Rashid et al., "Effect of pH and Temperature on the Binding of Bilirubin to Human Erythrocyte Membranes", J. Biosci., Jun. 2000, vol. 25, No. 2; pp. 157-161.
Gonzalez et al., "Standard Reference Material® 916a", National Institute of Standards & Technology, Certificate of Analysis, Aug. 22, 2016, pp. 1-5.

* cited by examiner

*Primary Examiner* — Maureen Wallenhorst

(57) ABSTRACT

A composition of a bilimbin stock and a method of preparation are provided. In one aspect of the invention, the composition includes a base solution. The composition further includes a carbonate salt. Additionally, the composition includes bilimbin. Furthermore, the composition includes human serum albumin.

16 Claims, 7 Drawing Sheets

COMPOSITION OF A BILIRUBIN STOCK AND A METHOD OF PREPARATION THEREOF

The subject application claims benefit under 35 USC § 119(e) of U.S. provisional Application No. 62/716,557, filed Aug. 9, 2018. The entire contents of the above-referenced patent application are hereby expressly incorporated herein by reference.

FIELD OF TECHNOLOGY

The present disclosure relates to the field of a composition of a chemical compound and more particularly to the field of a composition of a high concentration of bilirubin stock.

BACKGROUND

Bilirubin is a compound that forms a part of the metabolic pathway in human beings. Bilirubin is a degradation product of heme component of hemoglobin that is formed during the catabolism of red blood cells (RBC). Bilirubin may be one of the essential components that acts as an interferent in hemolysis studies. Bilirubin solution forms an essential part of a calibration process in hemolysis detection. Bilirubin solution may be used as standard samples of varying known concentrations, so as to calibrate a device configured to determine hemolysis in a whole blood sample. Due to photosensitive nature of bilirubin, it is essential that the handling of bilirubin be performed in dark or low light exposure conditions and variability in the prepared solution be minimal. Commercially available unconjugated form of bilirubin is soluble in organic solvents such as chloroform or dimethyl sulfoxide (DMSO). Such unconjugated bilirubin is insoluble in water. Organic solvents may compromise the analysis of the sample, for example, by damaging the sample and corroding the equipment used in the analysis. The fumes emitted by the organic solvent may also alter the surrounding environment. As organic solvents are mostly hazardous, hygroscopic and volatile in nature, the sample handling process may become more difficult.

The object of the invention is achieved by a composition of a bilirubin stock, a method, a process, and a kit for preparation of a bilirubin stock.

SUMMARY

A composition of a bilirubin stock is disclosed. In one aspect of the invention, the composition includes a base solution. The composition further includes a carbonate salt. Additionally, the composition includes bilirubin and human serum albumin, wherein the composition of carbonate salt, bilirubin and human serum albumin with respect to the base solution is in the ratio of 4.5:1:7.

In another aspect, a method of preparing a bilirubin stock includes dissolving 4.5 parts of a carbonate salt in a base solution to form a first solution. The method further includes controlling the pH of the first solution such that the pH is in a range of 11 to 12. Additionally, the method includes dissolving one part of bilirubin in the pH controlled first solution to obtain a second solution. Furthermore, the method includes dissolving 7 parts of human serum albumin in the base solution to obtain a third solution. The method also includes controlling the pH of the second solution such that the pH is in a range of 7 to 8. The method further includes adding the third solution to the pH controlled second solution to obtain the bilirubin stock.

In yet another aspect, a process of preparing a bilirubin stock includes controlling a pH of a first solution to be in range of 11 to 12. The process further includes dissolving bilirubin in the first solution to obtain a second solution. Additionally, the process includes dissolving human serum albumin in a base solution to obtain a third solution. The process also includes controlling the pH of the second solution to be in a range of 7 to 8. Furthermore, the process includes adding a portion of the third solution to the second solution to obtain the bilirubin stock.

In a further aspect of the invention, a kit for preparing a bilirubin stock includes a base solution. The kit further includes a first solution. Additionally, the kit includes bilirubin. Furthermore, the kit includes human serum albumin.

This summary is provided to introduce a selection of concepts in a simplified form that are further described below in the following description. It is not intended to identify features or essential features of the claimed subject matter. Furthermore, the claimed subject matter is not limited to implementations that solve any or all disadvantages noted in any part of this disclosure.

BRIEF DESCRIPTION OF THE DRAWINGS

The present invention is further described hereinafter with reference to illustrated embodiments shown in the accompanying drawings, in which.

DETAILED DESCRIPTION

Hereinafter, embodiments for carrying out the present invention are described in detail. The various embodiments are described with reference to the drawings, wherein like reference numerals are used to refer to like elements throughout. In the following description, for purpose of explanation, numerous specific details are set forth in order to provide a thorough understanding of one or more embodiments. It may be evident that such embodiments may be practiced without these specific details. In other instances, well known materials or methods have not been described in detail in order to avoid unnecessarily obscuring embodiments of the present disclosure. While the disclosure is susceptible to various modifications and alternative forms, specific embodiments thereof are shown by way of example in the drawings and will herein be described in detail. It should be understood, however, that there is no intent to limit the disclosure to the particular forms disclosed, but on the contrary, the disclosure is to cover all modifications, equivalents, and alternatives falling within the spirit and scope of the present disclosure.

Conventionally, bilirubin solution is prepared in small volumes with low concentration such that the stability of the bilirubin is maintained. Therefore, the object of the invention is to provide a composition of a high concentration bilirubin stock and a method of preparing thereof that is stable and can be diluted with less or no variation in consistency.

Figure 1:
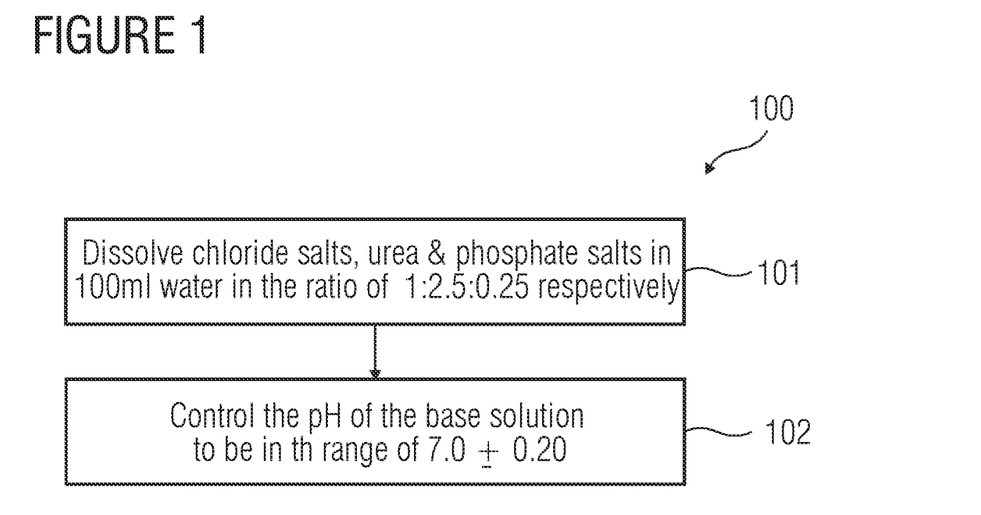
FIG. 1 illustrates a flowchart of an embodiment of a method of preparation of a base solution.

FIG. 1 illustrates a flowchart of an embodiment of a method 100 of preparing a base solution. The base solution includes one or more buffering agents that may naturally occur in a human body. These buffering agents enable dissolution of bilirubin, mimicking bilirubin dissolution in the human body. In an embodiment, the base solution is a bilirubin buffer. The one or more buffering agents may be, for example, one or more chloride salts; urea; and one or more phosphate salts. The chloride salts may include, for example, sodium chloride. The phosphate salts may include, for example, potassium phosphate, monobasic. In an embodiment, at step 101, the buffering agents are dissolved in 100 mL of purified water in the ratio of 1:2.5:0.25 respectively. Therefore, the base solution is an aqueous solution. For example, a 100 mL of the base solution is prepared by dissolving 1 g/dL of sodium chloride, 2.5 g/dL of urea and 0.25 g/dL of potassium phosphate monobasic in 80 mL of purified water in a volumetric flask. At step 102, the pH of the base solution is adjusted to 7.0±0.20. Once the buffering agents are dissolved, the volume is made up to 100 mL. The pH may be adjusted based on the actual pH of the prepared solution by adding 1N sodium hydroxide or 1N acetic acid to the base solution. In an embodiment, one or more preservatives may be added to the base solution so as to prevent bacterial or fungal growth in the base solution. The preservative that may be used includes, for example Supelco ProClin® 150, in the range of 200 μL to 400 μL.

Figure 2:
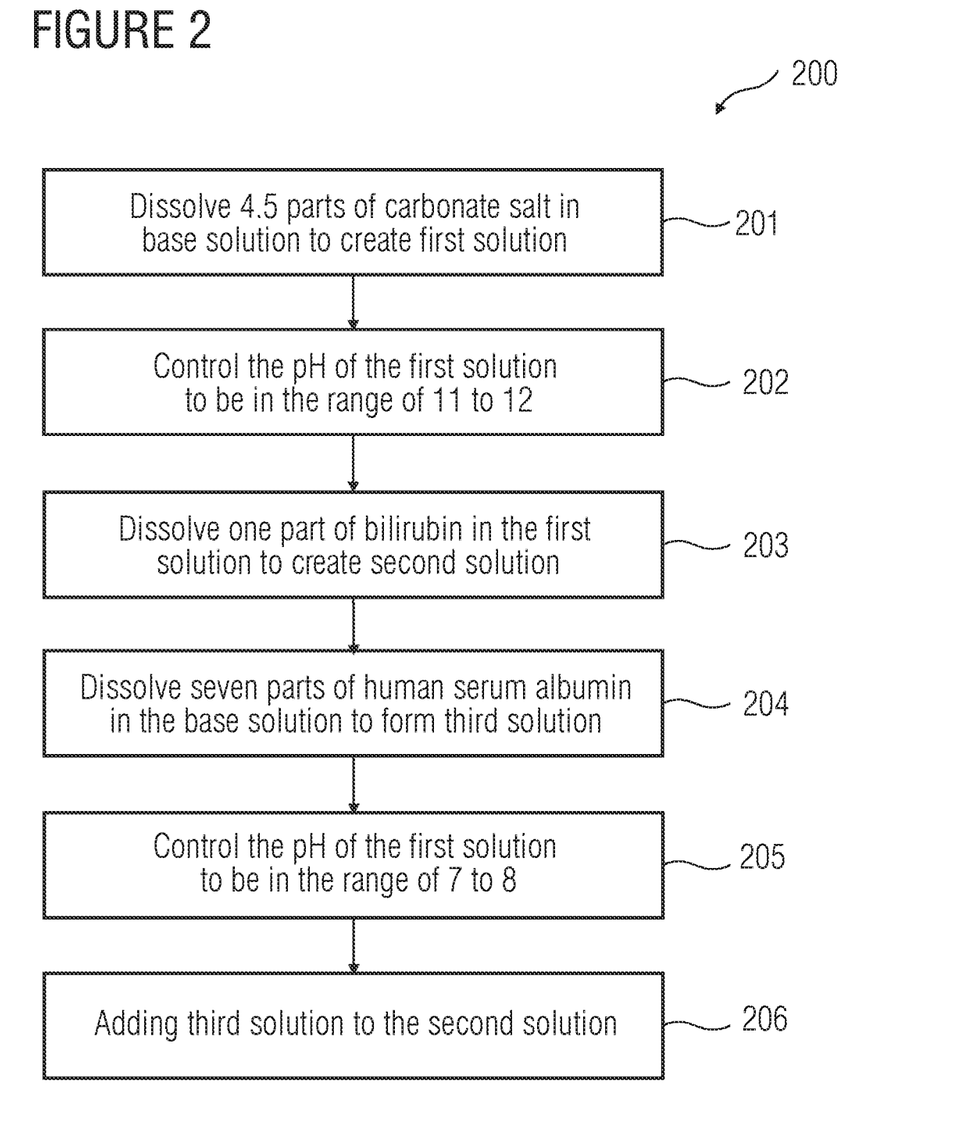
FIG. 2 illustrates a flowchart of an embodiment of a method of preparation of a bilirubin stock.

FIG. 2 illustrates a flowchart of an embodiment of a method 200 of preparing the bilirubin stock. At step 201, a first solution is created by dissolving a carbonate salt in the base solution. The carbonate salt may be, for example, sodium carbonate. At step 202, the pH of the first solution is controlled such that a pH range of 11 to 12 is achieved. At step 203, bilirubin is dissolved in the pH controlled first solution so as to form a second solution. In an embodiment, the bilirubin is in an unconjugated form. Bilirubin being acidic in nature reduces the pH of the first solution. Therefore, an alkaline pH is necessary is required to achieve dissolution of bilirubin in the first solution. Therefore, the pH of the first solution is increased so as to easily dissolve bilirubin in the first solution. At step 204, human serum albumin is dissolved in the base solution to create a third solution. Human serum albumin is found in human blood plasma and serum. Human serum albumin acts as a carrier molecule for unconjugated bilirubin, thereby enabling transportation of bilirubin. At a high pH of the second solution, bilirubin may precipitate. This is avoided by the presence of human serum albumin. At step 205, the pH of the second solution is controlled so as to be in the range of 7 to 8. The pH of the second solution may be reduced because human serum albumin may not be stable at an alkaline pH. At step 206, the third solution is added to the second solution, thereby stabilizing the bilirubin and achieving the bilirubin stock. Therefore, in a 100 mL of the base solution, the carbonate salt, bilirubin and human serum albumin is present in the ratio of 4.5:1:7. In an embodiment, filtered plasma may be added to the bilirubin stock. Addition of filtered plasma extends the stability of the bilirubin stock. Such filtered plasma may be added in the ratio of 1:1 to the bilirubin stock.

Example Embodiment 4.4 mg of sodium carbonate per mg of bilirubin is dissolved in 3 mL of the base solution, at a pH of 7.0±0.20, thereby creating the first solution. The pH of the first solution is controlled so as to be in the range of 11.5±0.02. The pH may be controlled, for example, using 1N sodium hydroxide. 28 mg of bilirubin is added to the first solution to create a second solution. On addition of bilirubin, the solution is stirred at a range of 200 to 300 revolutions per minute (rpm) using a magnetic stirrer, for a time period of 40 to 70 minutes. Constant stirring of the solution enables dissolution of bilirubin in the first solution, thereby forming the second solution. The pH of the first solution is maintained at 11.5±0.02 until bilirubin is dissolved completely. 40 mg/mL human serum albumin is dissolved in 5 mL of the base solution at pH 7.0±0.20, such that the concentration of human serum albumin is 200 mg/mL. This forms the third solution. The third solution may be sterilized, for example, using a 0.45 μm of syringe filter. The pH of the third solution may be maintained at 7.0. In the next step, the pH of the second solution is controlled from 11.5±0.02 to 7.4±0.20, for example, using 1N acetic acid. One mL of the third solution is added to the pH controlled second solution such that a final concentration of 40 mg/mL of human serum albumin is achieved. The volume may be made up to 5 mL using the base solution with a pH range of 7.3±0.1 using, for example, 1N acetic acid. This pH range of 7.3±0.1 mimics the physiological pH of a human being. The concentration of the bilirubin in the bilirubin stock may be in the range of 500 to 600 mg/dL. Equal volume of the bilirubin stock may be diluted with equal volume of plasma so as to obtain stocks of varied concentrations.

Figure 3:
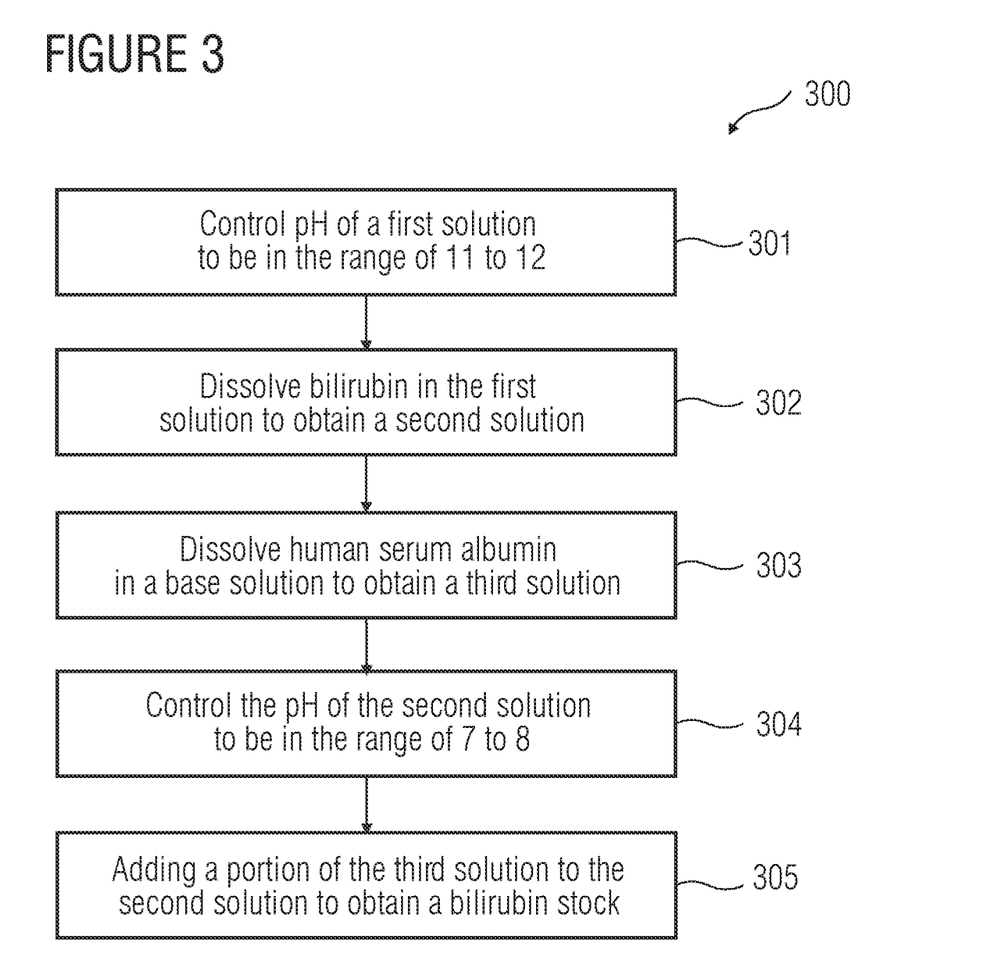
FIG. 3 illustrates a flowchart of an embodiment of a process of preparation of a bilirubin stock.

FIG. 3 illustrates a flowchart of an embodiment of a process 300 of preparing a bilirubin stock. At step 301, a pH of the first solution is controlled to be in the range of 11 to 12. In an embodiment, the first solution includes a carbonate salt dissolved in the base solution. The carbonate salt may be, for example, sodium carbonate. The pH of the first solution may be controlled, for example, using 1N sodium hydroxide or 1N acetic acid. At step 302, bilirubin is dissolved in the first solution so as to obtain a second solution. Dissolution of bilirubin in the first solution may be achieved by constant stirring, for example, using a magnetic stirrer. The pH of the first solution may be maintained in the range of 11 to 12 until the bilirubin dissolves completely to form the second solution. At step 303, human serum albumin is dissolved in the base solution so as to obtain a third solution. At a highly alkaline pH, the bilirubin may precipitate. The presence of human serum albumin may control or eliminate precipitation of bilirubin. However, human serum albumin may be unstable at an alkaline pH. Therefore, at step 304, the pH of the second solution is controlled so as to be in the range of 7 to 8. The pH of the second solution may be controlled, for example, using 1N acetic acid. Once the pH of the second solution is controlled to be in the neutral range, at step 305, a portion of the third solution is added to the second solution to obtain the bilirubin stock.

Figure 4:
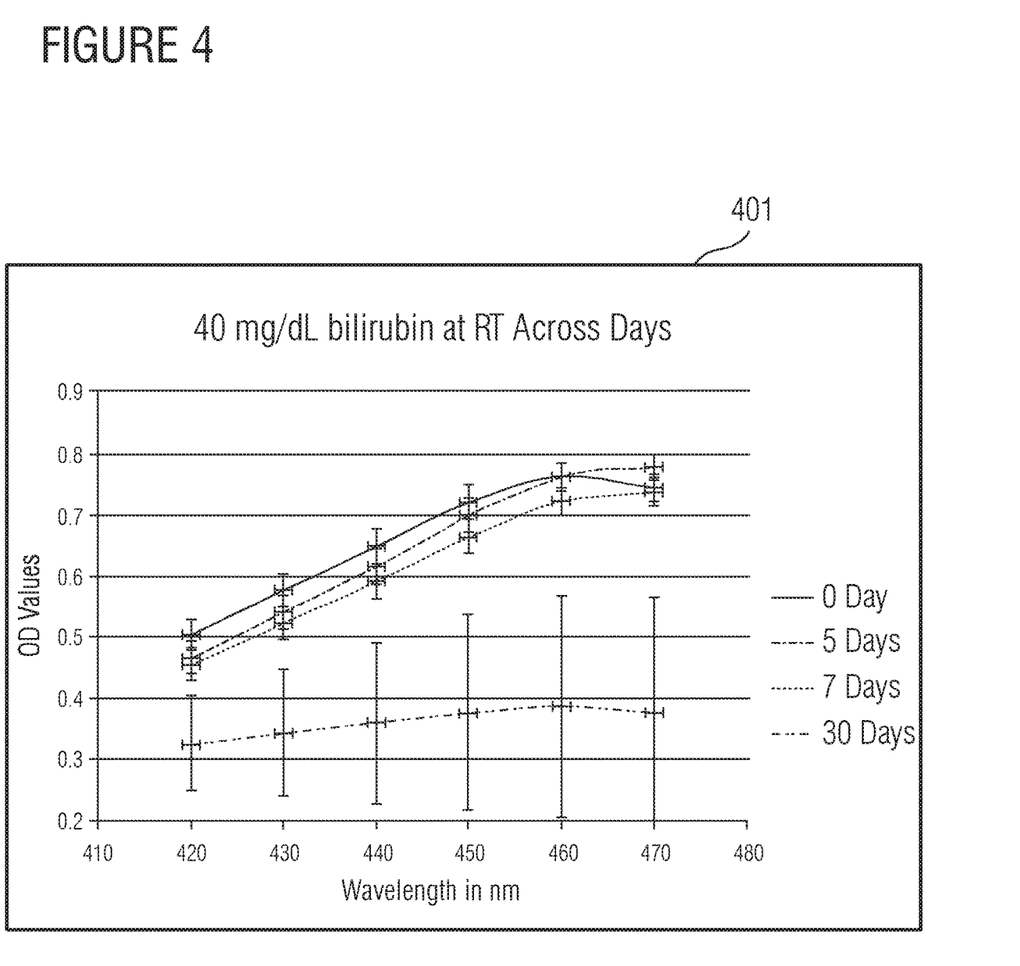
FIG. 4-7 illustrate a set of graphical representations depicting the stability of the bilirubin stock at varying temperatures, across days.
Figure 5:
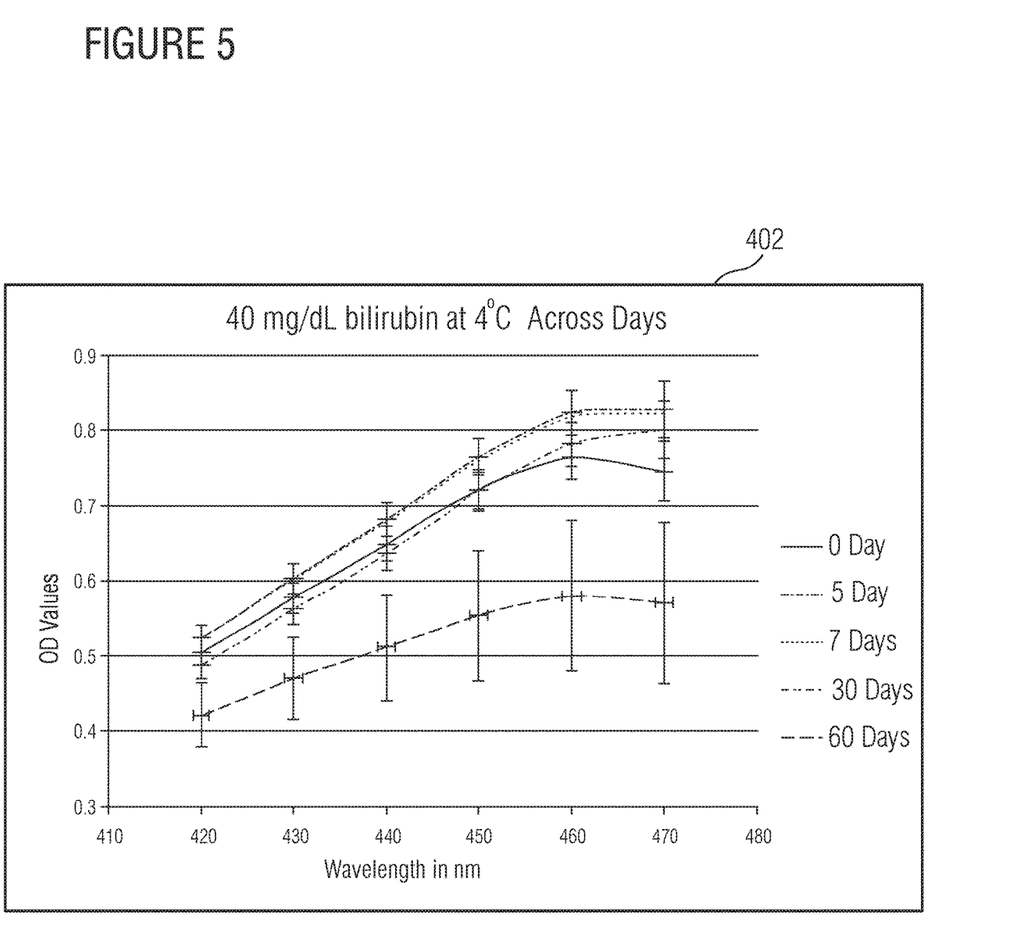
Figure 6:
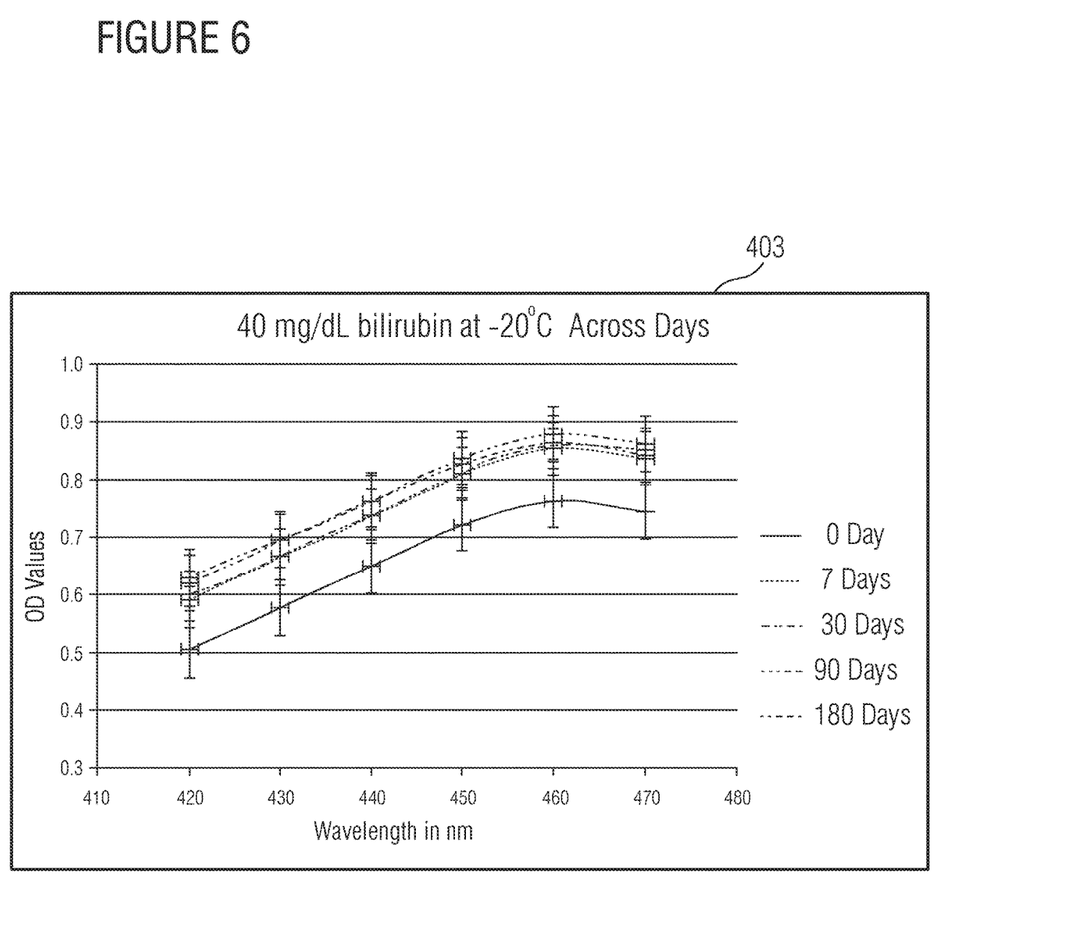
Figure 7:
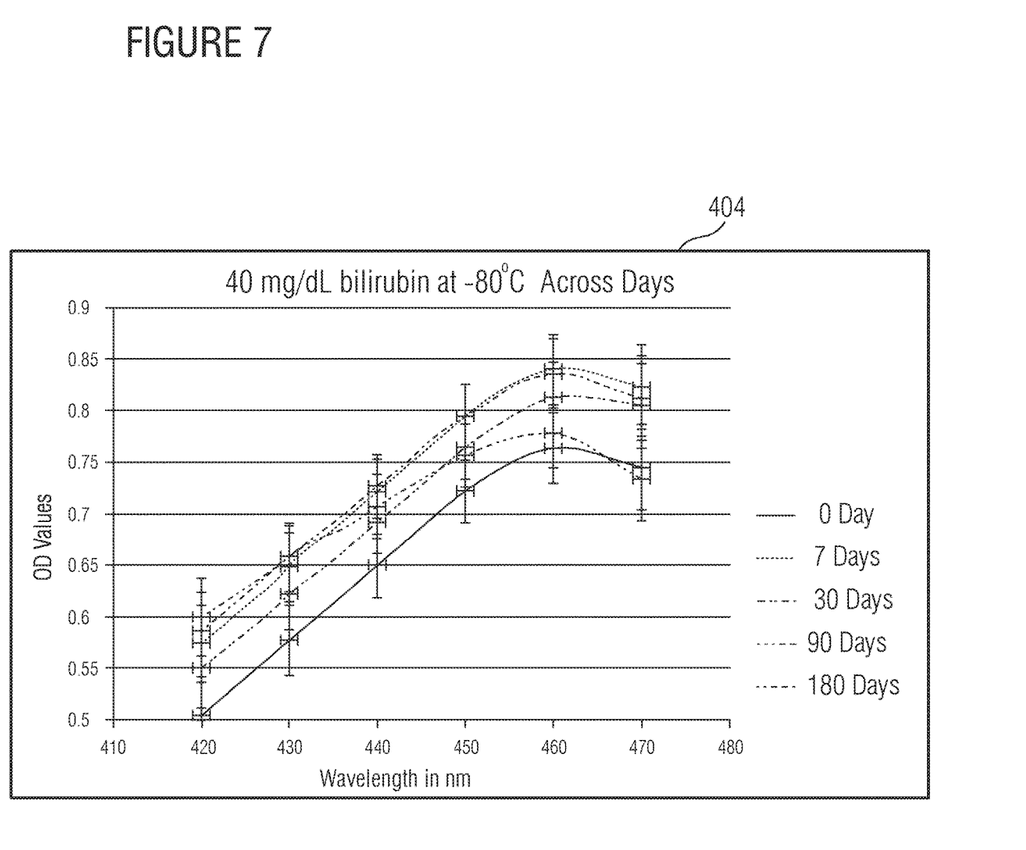

In an embodiment a standard curve and linearity of the bilirubin stock may be tested, for example, by obtaining optical density values using light having a wavelength range of 410 nm to 480 nm. Stability studies were performed for the bilirubin stock solution having a concentration of 40 mg/dL at varying temperatures, across days. The stability of the stock was checked at days 0, 5, 7, 30, 60, 90, 120, 150 and 180 by obtaining optical density values at wavelength range of 410 nm to 480 nm. FIG. 4 illustrates a set of graphical representations 401, 402, 403 depicting the stability of the bilirubin stock having a concentration of 40 mg/dL. The graph 401 depicts the stability of the bilirubin stock at room temperature. The bilirubin stock was prepared strictly in a dark environment or in low light exposure. The bilirubin stock so prepared was stored in dark, amber colored tubes so as to avoid photo-degradation. For purposes of brevity, the graph depicts stability data for days 0, 5, 7 and 30. The vertical bars in the graph 401 depict the average standard deviation of the optical density at each wavelength, across days.

From the graph 401, it is observed from the standard deviation values that at room temperature, the bilirubin stock remains stable for a period of 5 days. Beyond 5 days, the bilirubin stock degrades and may be unstable for use. The graph 402 depicts the stability of the bilirubin stock at 4° C. For the purposes of brevity, the graph 402 depicts stability data obtained at days 0, 5, 7, 30 and 60. The vertical bars in the graph 402 depict the average standard deviation of the optical density at each wavelength, across days. From the graph 402, it is observed from the standard deviation values that at 4° C., the bilirubin stock remains stable for a period of 30 days. Beyond 30 days, the bilirubin stock degrades and may be unstable for use. The graph 403 depicts the stability of the bilirubin stock at −20° C. For the purposes of brevity, the graph 403 depicts stability data obtained at days 0, 7, 30, 90 and 180. The vertical bars in the graph 403 depict the average standard deviation of the optical density at each wavelength, across days. From the graph 403, it is observed from the standard deviation values that at −20° C., the bilirubin stock remains stable for a period of 180 days. Therefore, long storage of bilirubin may be achieved at −20° C. The graph 404 depicts the stability of the bilirubin stock at −80° C. For the purposes of brevity, the graph 404 depicts stability data obtained at days 0, 7, 30, 90 and 180. The vertical bars in the graph 404 depict the average standard deviation of the optical density at each wavelength, across days. From the graph 404, it is observed from the standard deviation values that at −80° C., the bilirubin stock remains stable for a period of 180 days.

The instant teachings also provide kits designed to expedite performance of the subject methods. Kits serve to expedite the performance of the methods of interest by assembling two or more components required for carrying out the disclosed methods. Kits may contain components in pre-measured unit amounts to minimize the need for measurements by end-users. Kits may include instructions for performing one or more of the disclosed methods and processes. Preferably, the kit components are optimized to operate in conjunction with one another.

In an embodiment, the kit includes the base solution for dissolving bilirubin and human serum albumin. The kit further includes the first solution. The first solution may include a carbonate salt dissolved in the base solution. The carbonate salt may be, for example, sodium carbonate. The kit further includes bilirubin and human serum albumin. The bilirubin may be dissolved in the base solution to obtain the second solution and the human serum albumin may be dissolved in the base solution to obtain the third solution. A part of the third solution may be added to the second solution to obtain the bilirubin stock. In an alternate embodiment, the kit may further include one or more pH controlling reagents such as sodium hydroxide and/or acetic acid. The pH controlling reagents may be used to control the pH of the first solution, the second solution and/or the third solution.

Advantageously, the base solution is an aqueous solution. Therefore, the invention achieves dissolution of unconjugated bilirubin in the aqueous solution. The use of the water soluble, aqueous base solution instead of organic solvents reduces hazard level in preparation of bilirubin stock. Additionally, the protocol for handling the bilirubin stock is easier. Use of human serum albumin and human blood plasma mimics the stability of unconjugated form of bilirubin in a human being. Yet another advantage of the invention is that high concentration of bilirubin stock improves the ease of reconstitution of bilirubin at any desired concentration. This increases the dynamic working range of bilirubin for analysis of samples. Reconstitution of bilirubin from a high concentration bilirubin stock reduces daily turnaround time. Any day-to-day variation that may arise due to difference in preparation of stock solution is eliminated. Furthermore, preparation of the bilirubin stock may also be scaled up for commercial production.

The foregoing examples have been provided merely for the purpose of explanation and are in no way to be construed as limiting of the present invention disclosed herein. While the invention has been described with reference to various embodiments, it is understood that the words, which have been used herein, are words of description and illustration, rather than words of limitation. Further, although the invention has been described herein with reference to particular means, materials, and embodiments, the invention is not intended to be limited to the particulars disclosed herein; rather, the invention extends to all functionally equivalent structures, methods and uses, such as are within the scope of the appended claims. Those skilled in the art, having the benefit of the teachings of this specification, may effect numerous modifications thereto and changes may be made without departing from the scope and spirit of the invention in its aspects.

The following is a list of non-limiting, illustrative embodiments of the inventive concept(s) described above:

(1) An illustrative composition of bilirubin stock, wherein the bilirubin stock comprises: a base solution; a carbonate salt; bilirubin; and human serum albumin.

(2) The illustrative composition of embodiemnt 1, wherein the composition of carbonate salt, bilirubin and human serum albumin with respect to the base solution is in the ratio of 4.5:1:7.

(3) The illustrative compositions of embodiments 1 and 2, wherein the bilirubin is unconjugated bilirubin.

(4) The illustrative composition of embodiment 1, wherein the base solution comprises one or more of chloride salts, phosphate salts, and urea.

(5) The illustrative composition of embodiment 4, wherein the chloride salt, urea, and phosphate salt, are in the ratio of 1:2.5:0.25.

(6) The illustrative compositions of any of the abovementioned embodiments, wherein the base solution is an aqueous solution.

(7) The illustrative compositions of any of the abovementioned embodiments, further comprising filtered plasma.

(8) An illustrative method of preparing a bilirubin stock, the method comprising: dissolving a carbonate salt in a base solution to form a first solution; controlling the pH of the first solution such that the pH is in a range of 11 to 12; dissolving bilirubin in the pH controlled first solution to obtain a second solution; dissolving human serum albumin in the base solution to obtain a third solution; controlling the pH of the second solution such that the pH is in a range of 7 to 8; and adding the third solution to the pH controlled second solution to obtain the bilirubin stock.

(9) The illustrative method of embodiment 8, wherein the composition of carbonate salt, bilirubin and human serum albumin with respect to the base solution is in the ratio of 4.5:1:7.

(10) The illustrative method of embodiments 8 and 9, wherein the bilirubin is unconjugated bilirubin.

(11) The illustrative method of embodiment 8, wherein the base solution comprises one or more of chloride salts, phosphate salts, and urea.

(12) The illustrative method of embodiment 11, wherein the chloride salt, urea, and phosphate salt are in the ratio of 1:2.5:0.25.

(13) The illustrative method of embodiment 8, further comprising adding filtered plasma to the bilirubin stock.

(14) An illustrative process of preparation of a bilirubin stock, the process comprising the steps of: controlling a pH of a first solution to be in range of 11 to 12; dissolving bilirubin in the first solution to obtain a second solution; dissolving human serum albumin in a base solution to obtain a third solution; controlling the pH of the second solution to be in a range of 7 to 8; and adding a portion of the third solution to the second solution to obtain the bilirubin stock.

(15) The illustrative process of embodiment 14, wherein the bilirubin is unconjugated bilirubin.

(16) The illustrative process of embodiment 14, wherein the first solution comprises a carbonate salt dissolved in the base solution.

(17) The illustrative process of embodiment 14, wherein the base solution comprises one or more of chloride salts, phosphate salts, and urea in the ratio of 1:0.25:2.5.

(18) The illustrative process of embodiments 14 and 16, wherein the composition of the carbonate salt, bilirubin and human serum albumin with respect to the base solution is in the ratio of 4.5:1:7.

(19) The illustrative process of embodiment 14, further comprising adding filtered plasma to the bilirubin stock.

(20) An illustrative kit for preparing a bilirubin stock, the kit comprising: a base solution; a first solution; bilirubin; and human serum albumin.

(21) The illustrative kit of embodiment 20, further comprising one or more pH controlling reagents.

(22) The illustrative kit of embodiment 20, wherein the first solution comprises a carbonate salt dissolved in the base solution.

What is claimed is:

1. A composition of bilirubin stock, wherein the bilirubin stock comprises:
   an aqueous base solution comprising at least one chloride salt, at least one phosphate salt, and urea;
   a carbonate salt;
   bilirubin;
   human serum albumin; and
   wherein a combination of the carbonate salt, bilirubin, and human serum albumin with respect to the base solution is in a ratio of 4.5:1:7 by weight.

2. The composition of claim 1, wherein the bilirubin is unconjugated bilirubin.

3. The composition of claim 1, wherein the at least one chloride salt, at least one phosphate salt, and urea are present in the base solution in a ratio of 1:2.5:0.25 by weight.

4. The composition of claim 1, further comprising filtered blood plasma.

5. A method of preparing a bilirubin stock, the method comprising:
   dissolving a carbonate salt in an aqueous base solution to form a first solution, wherein the aqueous base solution comprises at least one chloride salt, at least one phosphate salt, and urea;
   controlling a pH of the first solution such that the pH is in a range of 11 to 12;
   dissolving bilirubin in the pH controlled first solution to obtain a second solution;
   dissolving human serum albumin in the base solution to obtain a third solution;
   controlling a pH of the second solution such that the pH is in a range of 7 to 8; and
   adding the third solution to the pH controlled second solution to obtain the bilirubin stock.

6. The method of claim 5, wherein a combination of the carbonate salt, bilirubin and human serum albumin with respect to the base solution is in a ratio of 4.5:1:7 by weight.

7. The method of claim 5, wherein the bilirubin is unconjugated bilirubin.

8. The method of claim 5, wherein the at least one chloride salt, at least one phosphate salt, and urea are present in the base solution in a ratio of 1:2.5:0.25, respectively, by weight.

9. The method of claim 5, further comprising adding filtered blood plasma to the bilirubin stock.

10. A process of preparation of a bilirubin stock, the process comprising the steps of:
    controlling a pH of a first solution to be in a range of 11 to 12, wherein the first solution comprises a carbonate salt;
    dissolving bilirubin in the first solution to obtain a second solution;
    dissolving human serum albumin in an aqeuous base solution to obtain a third solution, wherein the aqueous base solution comprises at least one chloride salt, at least one phosphate salt, and urea;
    controlling a pH of the second solution to be in a range of 7 to 8; and
    adding a portion of the third solution to the second solution to obtain the bilirubin stock.

11. The process of claim 10, wherein the bilirubin is unconjugated bilirubin.

12. The process of claim 10, wherein the first solution comprises a carbonate salt dissolved in the base solution.

13. The process of claim 10, wherein the at least one chloride salt, at least one phosphate salt, and urea are present in the base solution at a ratio of 1:2.5:0.25, respectively, by weight.

14. The process of claim 10, wherein a combination of the carbonate salt, bilirubin and human serum albumin with respect to the base solution is in a ratio of 4.5:1:7 by weight.

15. The process of claim 10, further comprising adding filtered blood plasma to the bilirubin stock.

16. A kit for preparing a bilirubin stock, the kit comprising:
    an aqueous base solution comprising at least one chloride salt, at least one phosphate salt, and urea present at a ratio of 1:2.5:0.25, respectively, by weight;
    a first solution, wherein the first solution comprises a carbonate salt;
    bilirubin; and
    human serum albumin.

* * * * *